US006992758B2

(12) United States Patent
Kaplan et al.

(10) Patent No.: US 6,992,758 B2
(45) Date of Patent: Jan. 31, 2006

(54) BIREFRINGENCE MEASUREMENT OF LARGE-FORMAT SAMPLES

(75) Inventors: Andrew D. Kaplan, Portland, OR (US); James C. Mansfield, Hillsboro, OR (US); Douglas C. Mark, Tigard, OR (US)

(73) Assignee: Hinds Instruments, INC, Hillsboro, OR (US)

( * ) Notice: Subject to any disclaimer, the term of this patent is extended or adjusted under 35 U.S.C. 154(b) by 51 days.

(21) Appl. No.: 10/359,529

(22) Filed: Feb. 5, 2003

(65) Prior Publication Data

US 2004/0075834 A1    Apr. 22, 2004

Related U.S. Application Data

(60) Provisional application No. 60/419,685, filed on Oct. 16, 2002.

(51) Int. Cl.
 *G01N 21/01*    (2006.01)
(52) U.S. Cl. ........................................ 356/244; 356/365
(58) Field of Classification Search ................ 356/244, 356/365, 369, 239.1–239.3, 429–430, 364, 356/245, 246, 440, 442
See application file for complete search history.

(56) References Cited

U.S. PATENT DOCUMENTS

| | | | | |
|---|---|---|---|---|
| 3,759,620 A | * | 9/1973 | Cushing et al. ............. 356/430 |
| 3,925,049 A | * | 12/1975 | Schwenninger ............. 356/430 |
| 4,313,679 A | * | 2/1982 | Wolff et al. ................. 356/244 |
| 5,047,652 A | * | 9/1991 | Lisnyansky et al. ........ 356/429 |
| 5,201,141 A | * | 4/1993 | Ahm ............................. 47/67 |
| 5,400,258 A | * | 3/1995 | He ............................. 356/429 |
| 5,470,757 A | * | 11/1995 | Gagnon et al. ............. 436/164 |
| 5,504,581 A | * | 4/1996 | Nagata et al. .............. 356/364 |
| 5,519,218 A | * | 5/1996 | Chang .................... 250/339.07 |
| 5,526,119 A | * | 6/1996 | Blit et al. .................... 356/402 |
| 5,805,291 A | * | 9/1998 | Calvin et al. ................ 356/429 |
| 5,858,452 A | * | 1/1999 | Leader et al. ................. 427/97 |
| 5,898,181 A | * | 4/1999 | Vurens .................. 250/559.28 |
| 5,916,425 A | * | 6/1999 | Leader et al. ............... 204/416 |
| 6,061,131 A | * | 5/2000 | Igushi et al. ................ 356/336 |
| 6,111,651 A | * | 8/2000 | Shakespeare ............... 356/429 |
| 6,141,867 A | * | 11/2000 | Fukada et al. ................ 29/747 |
| 6,317,209 B1 | * | 11/2001 | Priestly ....................... 356/365 |

\* cited by examiner

*Primary Examiner*—Layla G. Lauchman
(74) *Attorney, Agent, or Firm*—Ipsolon LLP

(57) ABSTRACT

The disclosure is directed to systems and methods for precisely measuring birefringence properties of large-format samples of optical elements. A gantry-like configuration is employed for precise movement of birefringence measurement system components relative to the sample. There is also provided an effective large-format sample holder that adequately supports the sample to prevent induced birefringence therein while still presenting a large area of the sample to the unhindered passage of light.

16 Claims, 4 Drawing Sheets

BIREFRINGENCE MEASUREMENT OF LARGE-FORMAT SAMPLES

This application claims the benefit of U.S. Provisional Application No. 60/419,685 filed Oct. 16, 2002.

TECHNICAL FIELD

This application relates to measurement of birefringence properties of optical elements, and primarily to large-format elements, such as large sheets of material used for liquid crystal displays (LCDs).

BACKGROUND

Many important optical materials exhibit birefringence. Birefringence means that different linear polarizations of light travel at different speeds through the material. These different polarizations are most often considered as two components of the polarized light, one component being orthogonal to the other. Birefringence is an intrinsic property of many optical materials, and may also be induced by external forces applied to the material.

Retardation or retardance represents the integrated effect of birefringence acting along the path of a light beam traversing the sample. If the incident light beam is linearly polarized, two orthogonal components of the polarized light will exit the sample with a phase difference, called the retardance. The fundamental unit of retardance is length, such as nanometers (nm). It is frequently convenient, however, to express retardance in units of phase angle (waves, radians, or degrees), which is proportional to the retardance (nm) divided by the wavelength of the light (nm). An "average" birefringence for a sample is sometimes computed by dividing the measured retardation magnitude by the thickness of the sample.

Oftentimes, the term "birefringence" is interchangeably used with and carries the same meaning as the term "retardance." Thus, unless stated otherwise, those terms are also interchangeably used below.

The two orthogonal polarization components described above are parallel to two orthogonal axes, which referred to as the "fast axis" and the "slow axis" of the optical material. The fast axis is the axis of the material that aligns with the faster moving component of the polarized light through the sample. Therefore, a complete description of the retardance of a sample along a given optical path requires specifying both the magnitude of the retardance and its relative angular orientation of the fast (or slow) axis of the sample.

The need for precise measurement of birefringence properties has become increasingly important in a number of technical applications. For instance, it is important to specify linear birefringence in optical elements that are used in high-precision instruments employed in semiconductor and other industries.

Moreover, some applications require that the retardation measurements be made across the surface of large-format optical elements or samples. For example, a manufacturer may wish to examine the retardance across the area of a large sheet of such material, thereby to determine whether the material is satisfactory (from a birefringence standpoint) before incurring further expense in processing the panel into a plurality of units.

The measurement of the birefringence across such large-format samples raises problems relating to the precise handling of the sample and instrumentation that is employed for such measurement. For example, it is impractical to move such large-format samples relative to the birefringence measurement instrument. Instead, the necessary optical components of the system can be moved relative to a stationary sample. One problem that arises with such a system is the need to ensure that components of the birefringence measurement system move precisely relative to one another and relative to the sample, thereby to provide consistently accurate birefringence measurement data irrespective of the amount the system components need to be moved in traversing large-format samples.

As noted above, external forces acting on the optical element or sample can induce birefringence. Such forces arise, for example, when a sample is bent or otherwise stressed while being held. The mass of the sample can induce some birefringence as a result of gravitational force, especially in instances where the sample is oriented with a significant amount of its mass vertically aligned. Thus, accurate measurement of the intrinsic birefringence of large-format samples requires that the optical element or sample of concern be held or supported in a manner that does not induce birefringence in the sample, which would produce an erroneous measure of the intrinsic birefringence. Specifically, such support requires that a flat sample be substantially uniformly supported in a plane without stress applied to the sample.

In addition to the need for adequately supporting the sample in a plane, the mechanism for supporting the sample must permit the passage of a light beam through the sample without interfering with that beam. The unhindered passage of a light beam through the sample and to an associated detection assembly is a critical aspect of accurate birefringence measurement. Moreover, it is most often desirable to measure the birefringence of a sample at closely spaced locations across the area of the sample. The design for a large-format sample holder, therefore, must strike a balance between adequately supporting the sample to prevent stress-induced birefringence, while still presenting a large area of the sample to the unhindered passage of light for birefringence measurement.

Of course, the ease and cost of manufacture, as well as the requirements for shipping and assembling a birefringence measurement system that includes a large-format sample holder are also important design considerations.

SUMMARY OF THE INVENTION

The present invention is directed to systems and methods for precisely measuring birefringence properties of large-format samples of optical elements.

In one preferred embodiment, a gantry-like configuration is employed for precise Y-direction movement of birefringence measurement system components relative to the sample. The components are mounted for precise X-direction movement. Accordingly, the entire area of the sample is traversed by the birefringence measurement components.

There is also provided an effective large-format sample holder that adequately supports the sample to prevent induced birefringence therein while still presenting a large area of the sample to the unhindered passage of the light beam of the birefringence measurement system.

DETAILED DESCRIPTION

One embodiment of a system for measuring birefringence is described with reference to FIGS. 1 and 2. The system uses a dual photoelastic modulator (PEM) setup to measure low-level linear birefringence in optical elements. This embodiment determines the birefringence magnitude and angular orientation and has specifically designed signal processing, a data collection scheme, and an algorithm for measuring low-level linear birefringence at very high sensitivity.

Figure 1:
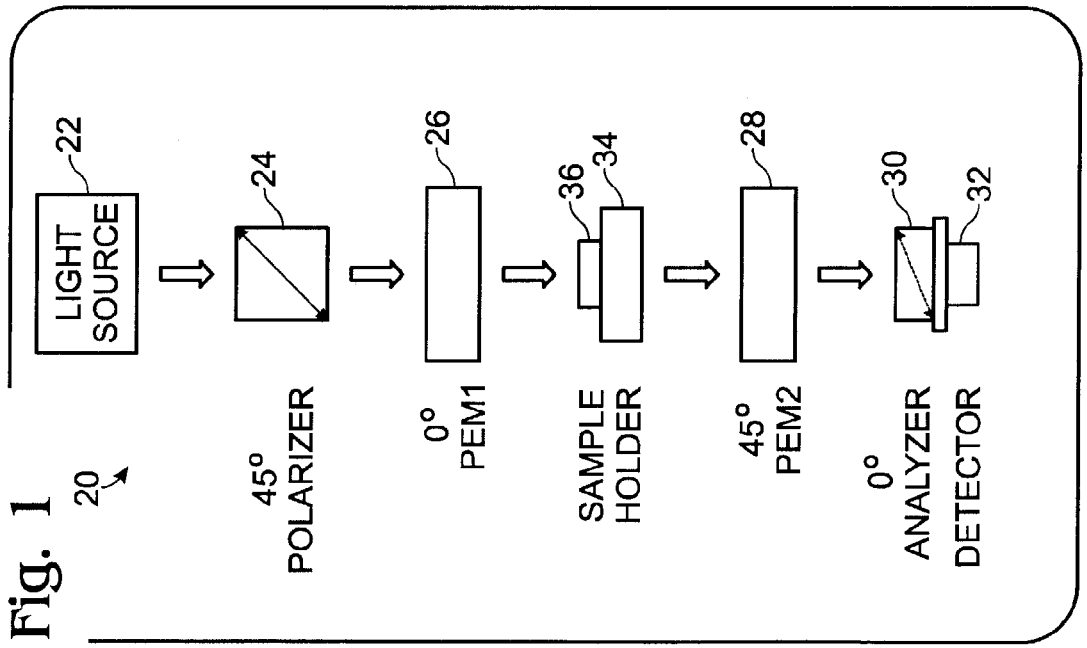
FIG. 1 is a diagram of one embodiment showing a preferred arrangement of the optical components of a birefringence measurement system that is used for measuring large-format optical elements in accordance with the present invention.

As shown in FIG. 1, the dual-PEM setup 20 of this embodiment contains two modules. The source module comprises a light source 22, a polarizer 24 oriented at 45 degrees, and a PEM 26 oriented at 0 degrees. The light source 22 is a polarized He—Ne laser that produces a beam having 632.8 nm wavelength and a spot size (diameter) of about 1 mm.

The detector module includes a second PEM 28 that is set to a modulation frequency that is different from the modulation frequency of the first PEM 26. The second PEM 28 is oriented at 45 degrees. The detector module also includes an analyzer 30 at 0 degrees and a detector 32.

Between the source and detector modules is a sample holder 34 (shown schematically in FIG. 1) that supports an optical element or sample 36 and is described more fully below. The vertically aligned arrows in FIG. 1 represent the path of a light beam emanating from the source 22 to pass through the sample 36 (as well as the other optical elements of the system) and into the detector 32.

With continued reference to FIG. 1, the polarizer 24 and analyzer 30 are each a Glan-Thompson-type. A Si-photodiode detector 32 is used in this embodiment. Both PEMs 26, 28 are bar-shaped, fused silica models having two transducers. The transducers are attached to the fused silica optical element with soft bonding material. To minimize birefringence induced in the optical element, only the transducers are mounted to the PEM housing. The two PEMs 26, 28 have nominal resonant frequencies of 50 and 55 KHz, respectively.

Figure 2:
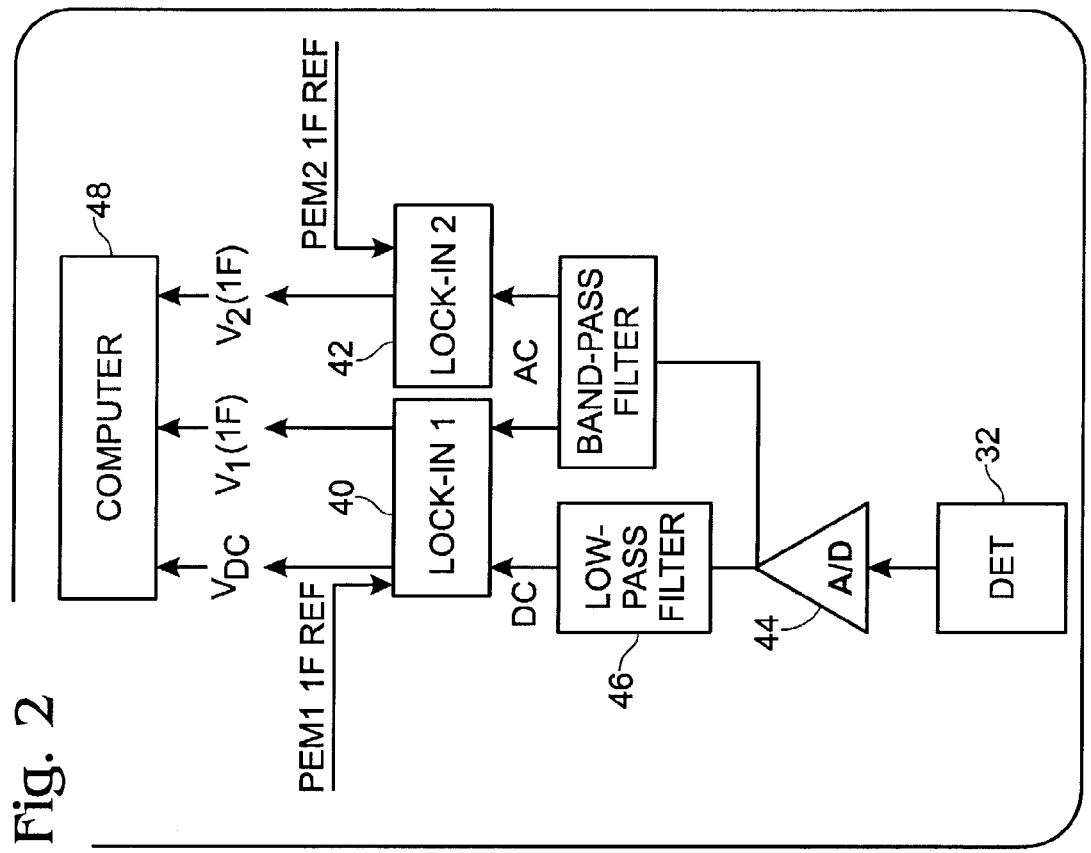
FIG. 2 is a block diagram of the signal processing components of the system depicted in FIG. 1.

With reference to FIG. 2, the electronic signals generated at the detector 32 contain both "AC" and "DC" signals and are processed differently. The AC signals are applied to two lock-in amplifiers 40, 42. Each lock-in amplifier, referenced at a PEM's fundamental modulation frequency (1F), demodulates the 1F signal provided by the detector 32. In a preferred embodiment, the lock-in amplifier is an EG&G Model 7265.

The DC signal is recorded after the detector signal passes through an analog-to-digital converter 44 and a low-pass electronic filter 46. The DC signal represents the average light intensity reaching the detector 32. The DC and AC signals are recorded at different PEM retardation settings.

The theoretical analysis underlying the measurement of the birefringence properties of the sample 36 in this embodiment is based on a Mueller matrix analysis and associated light-intensity signal processing to provide data representing the magnitude and angular orientation of the birefringence. Such processing does not form part of the present invention.

Figure 3:
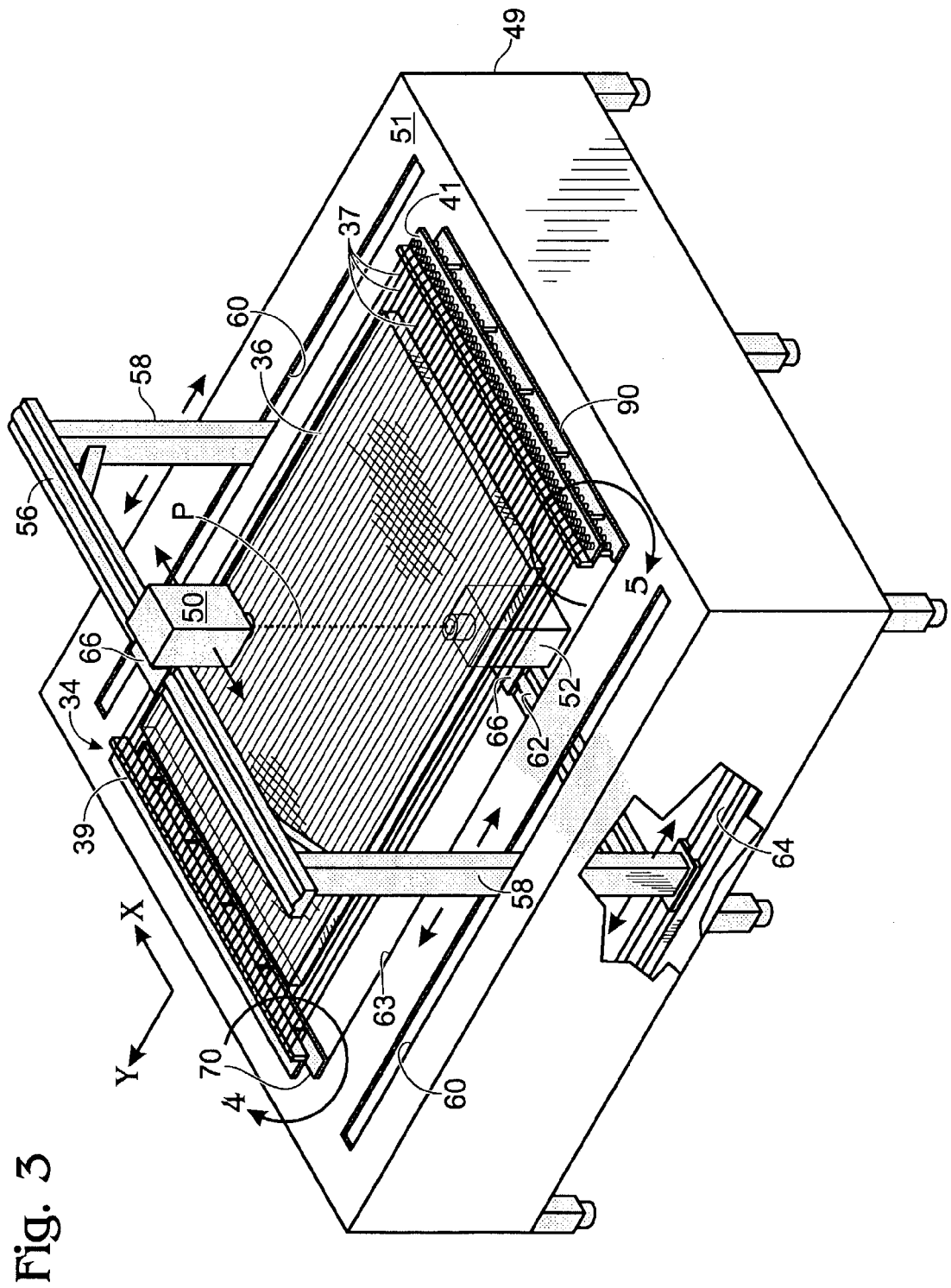
FIG. 3 illustrates one preferred apparatus for holding a large-format optical element (sample) and for securing and moving certain of the components of the system of FIGS. 1 and 2 for measuring the birefringence at locations across the area of the sample.

With reference to FIG. 3, the particulars of the large-format birefringence measurement system of the present invention are now described. The birefringence measurement system includes a cabinet 49 that has a top 51. The sample 36 is supported on the top 51 of the cabinet by the holder 34. The sample 36 is in a large format and may be, for example, a 1250 mm×1100 mm sheet of LCD material having a thickness of about 0.5 mm. The thickness of the sample is greatly exaggerated in FIG. 3.

The sample 36 remains stationary, supported by the holder 34. In one preferred embodiment, the holder comprises a plurality of spaced-apart, taut wires 37 strung between two support beam assemblies 39, 41, one beam assembly on either side of an opening 63 in the top surface of the cabinet. The particulars of the holder are described more fully below.

An optical path "P" is provided between a source module 50 and a detector module 52 (FIG. 3). The source module 50 is an encasement of the components that make up that module as described above, and the detector module 52, is an encasement of the above-described components that make up that module.

The source module 50 is mounted to an upper beam member 56 that spans, in an X-direction, the width of the sample holder 34 (hence, the sample 36). That upper beam member is supported at its opposite ends by vertical gantry columns 58. The beam member 56 is fastened to move with the columns in the Y-direction. Each column extends through an elongated clearance slot 60 formed near the side edges of the cabinet top 51.

The detector module 52 is mounted to a lower beam member 62 that is beneath the sample holder 34 and connected between (to move with) the gantry columns 58.

The slots 60 permit the gantry columns 58 to move in the Y-direction to span the length of the sample 36. To this end, the lower ends of the gantry columns are mounted to a matched pair of actuators 64 (only one seen in FIG. 3) such as a ballscrew linear actuator of sufficient length to traverse the length of the sample. Suitable position sensors and processor-controlled motors are also provided for ensuring synchronous movement of the gantry columns; hence uniform movement of the source and detector modules in the Y-direction.

The upper beam member 56 and lower beam member 62 are both configured to carry a servo motion control unit 66, to which each module 50, 52 is connected. The units 66 include suitable encoders, and associated motion controllers for ensuring that, as respects the X-direction motion, both modules 50, 52 move in unison.

It will be appreciated that the precisely controlled X-Y movement of the source and detector modules as described above ensures repeatable birefringence measurements. For example, such movement ensures that the optical path "P" will not change relative to the detector aperture, which change might otherwise introduce systematic errors into the birefringence measurement results.

Figure 4:
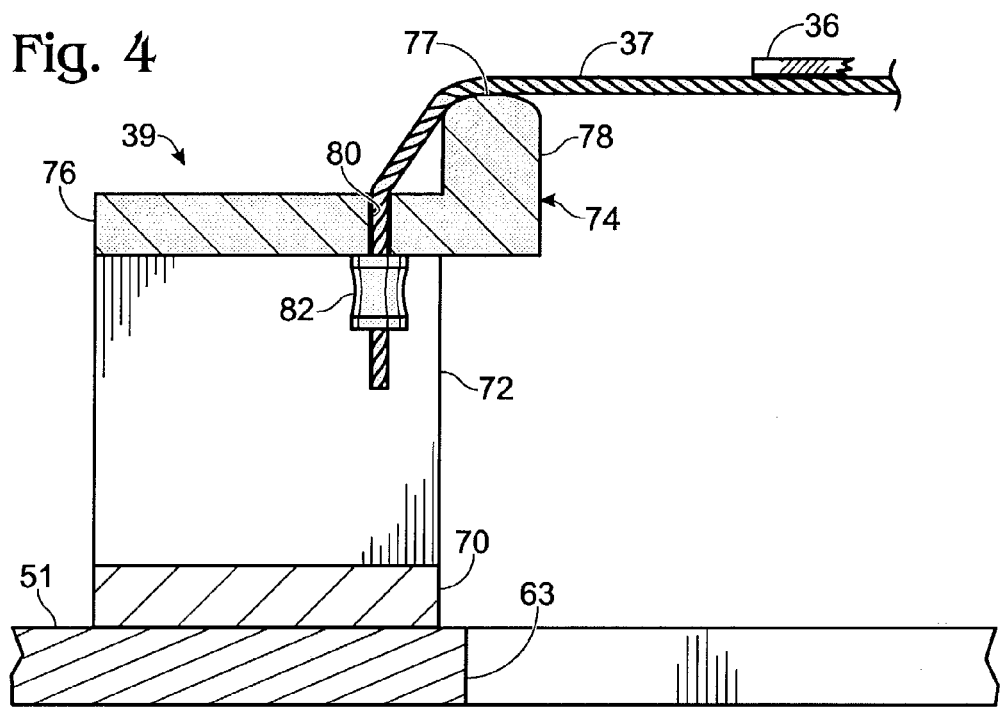
FIGS. 4 and 5 are enlarged, detailed sectional views of one part of the sample holder portion of the apparatus of FIG. 3.
Figure 5:
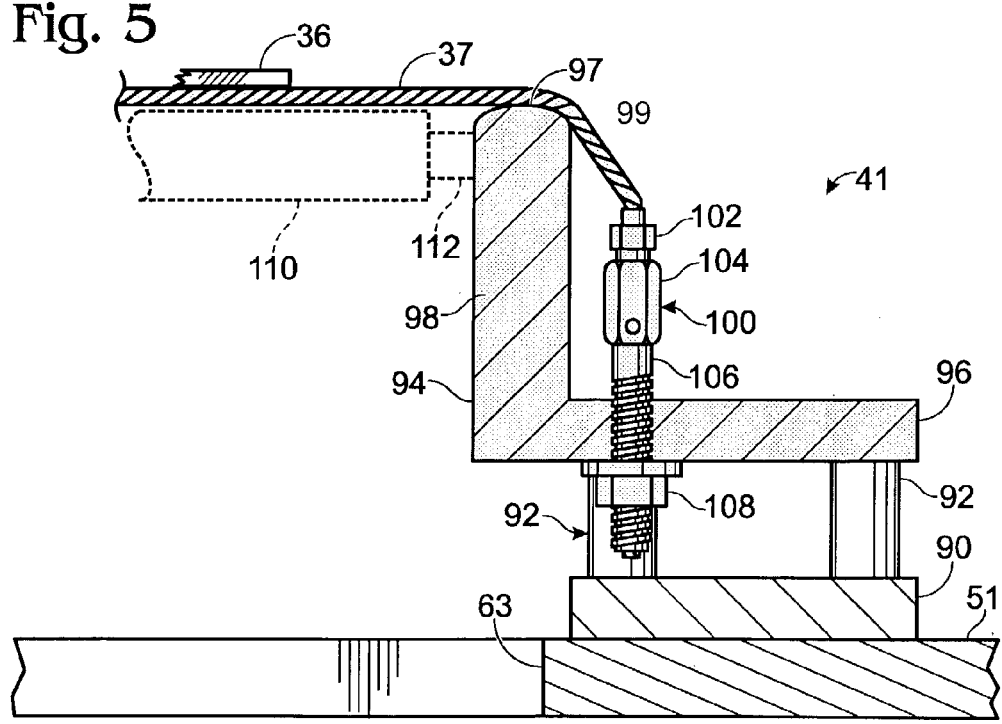

With reference to FIGS. 3–5, the holder 34 includes a fixed beam assembly 39 that includes a flat base plate 70 that is attached to the top 51 of the cabinet 49. The base plate 70 is attached near an edge of the opening 63 in the top 51. A number of spacer plates 72 (see FIG. 3) are fixed to the upper surface of the base plate 70 to extend therefrom and support an anchor plate 74 above the base plate 70. The anchor plate 74 is generally "L" shaped in cross section with a flat leg 76 and an up upwardly projecting flange 78. The underside of the leg 76 is fixed to the tops of the spacer plates 72. The uppermost edge 77 of the flange 78 is rounded.

One end of each of the wires 37 mentioned above is fixed to the anchor plate 74. In particular, the wire ends (only a single wire end appearing in FIGS. 4 and 5) pass through an aperture 80 made in the leg 76 and through a hollow, cylindrical stop sleeve 82. The sleeve 82 is crimped to fix the sleeve to the wire end and, since the sleeve diameter exceeds that of the aperture 80, the wire 37 can thereafter be tensed with the sleeve abutting the leg 76 of the anchor plate 74 to anchor the end of the wire. The wire 37 is drawn by the tension over the rounded edge 77 to the other beam assembly 41 described below.

In a preferred embodiment the wire 37 is stainless steel wire rope that may or may not be coated with low-friction coatings such as Teflon. Nylon-coated wire rope and a number of other materials may also be used for the wires.

Preferably, the diameter of the wire 37 is selected to be small enough (for example 1 or 2 mm) to minimize the amount of space across the window 63 that is occupied by the wires (and that will interfere with the light beam path "P," FIG. 3). The wire material and the uniform spacing between each wire is selected so that, depending on the weight of the sample, sufficient tension can be placed on each wire (as described more below) to ensure that the sample is held in a plane without any bending stress, which might be introduced if the sample were permitted to sag.

The spacing between individual wires 37 in the holder is as large as possible (depending upon the unit weight and flexibility of the sample) so that, as just mentioned, space across the window 63 that is occupied by the wires is minimized. The spacing between wires may be a few millimeters to several centimeters, depending, as mentioned, on the physical characteristics of the sample. Preferably, a minimum spacing (for example, 5 mm) is maintained to ensure that there remains between each wire a sufficiently large gap so that contaminants (glass particles, coatings debris etc.) that could interfere with the light beam do not become trapped between the wires.

In FIGS. 4 and 5 the thickness of the sample 36 is depicted in a scale that, unlike the relatively thick sample 36 shown in FIG. 1 for illustrative purposes, reflects the relatively thin nature of at least some types of samples that are used with the present holder 34, such as the 0.5 mm-thick LCD material mentioned above.

As shown in FIG. 5, the other end of each wire 37 is connected to the tension beam assembly 41 that permits the wire tension to be established and maintained. The tension beam assembly 41 includes a flat base plate 90 that is attached to the top 51 of the cabinet 49. The base plate 90 is attached near the edge of the opening 63 in the top 51. A number of cylindrical spacer posts 92 are fixed at spaced-apart intervals to the upper surface of the base plate 90 to extend therefrom and support an anchor plate 94 above the base plate 90. The anchor plate 94 is generally "L" shaped with a flat leg 96 and an up upwardly projecting flange 98. The underside of the leg 96 is fixed to the tops of the spacer posts 92. The uppermost edge 97 of the flange 98 is rounded.

The end of each of the wires 37 is pulled over the rounded edge 97 and connected to the leg 96 of the anchor plate 94 in a manner that both anchors the end and that permits the application of tension to the wire. One way for making this connection is to employ a conventional wire end fitting, such as a stud end fitting 100 shown in FIG. 5. The stud end fitting 100 captures the end of the wire in an externally threaded sleeve 102 that threads into a hex-ended stud 104. The threaded shaft 106 of the stud passes through an aperture in the leg 96 and through a lock nut 108 that bears against the underside of the leg. The nut is tightened once sufficient tension is placed on the wire 37.

The beam assemblies 39, 41 are configured and arranged so that the uppermost parts of the respective rounded edges 77, 97 (FIGS. 4 and 5) are in a common plane such that the taut wires 37 extending between those assemblies will hold the sample flat, without bending stress, thereby ensuring that the light beam passing through the sample is unaffected by birefringence that would otherwise be induced in the sample by such bending.

It will be appreciated that in the course of manufacturing the present holder, it is only necessary to ensure that the top edges 77, 97 of the beam assemblies are in a common plane and that suitable tension is placed on the wires to precisely maintain the flatness of the sample that the holder supports. This can be compared to the complexities of, for example, manufacturing a large, rigid, precisely flat support plate with openings machined therethrough for permitting the passage of light.

It is contemplated that, as an alternative to the taut wires 37, other thin elongated members may be employed. For example, as depicted in FIG. 5, small-diameter cylindrical rods 110 can span the window 63. In one such embodiment, the rods are rotatably mounted, as at bearings 112, between members like the above discussed anchors 74, 94 that are mounted to opposing edges of the window 63. The rotatable rods minimize the contact between the holder and the sample and also provide a way for easily rolling a sample onto and off the holder.

It is also contemplated that the sample holder could be constructed in a manner that permits a relatively rapid application of tension to the wires and a correspondingly rapid release, thereby to facilitate assembly and disassembly of the holder as may be desired for shipping. One embodiment directed to this aspect of the invention is illustrated in FIG. 6.

Figure 6:
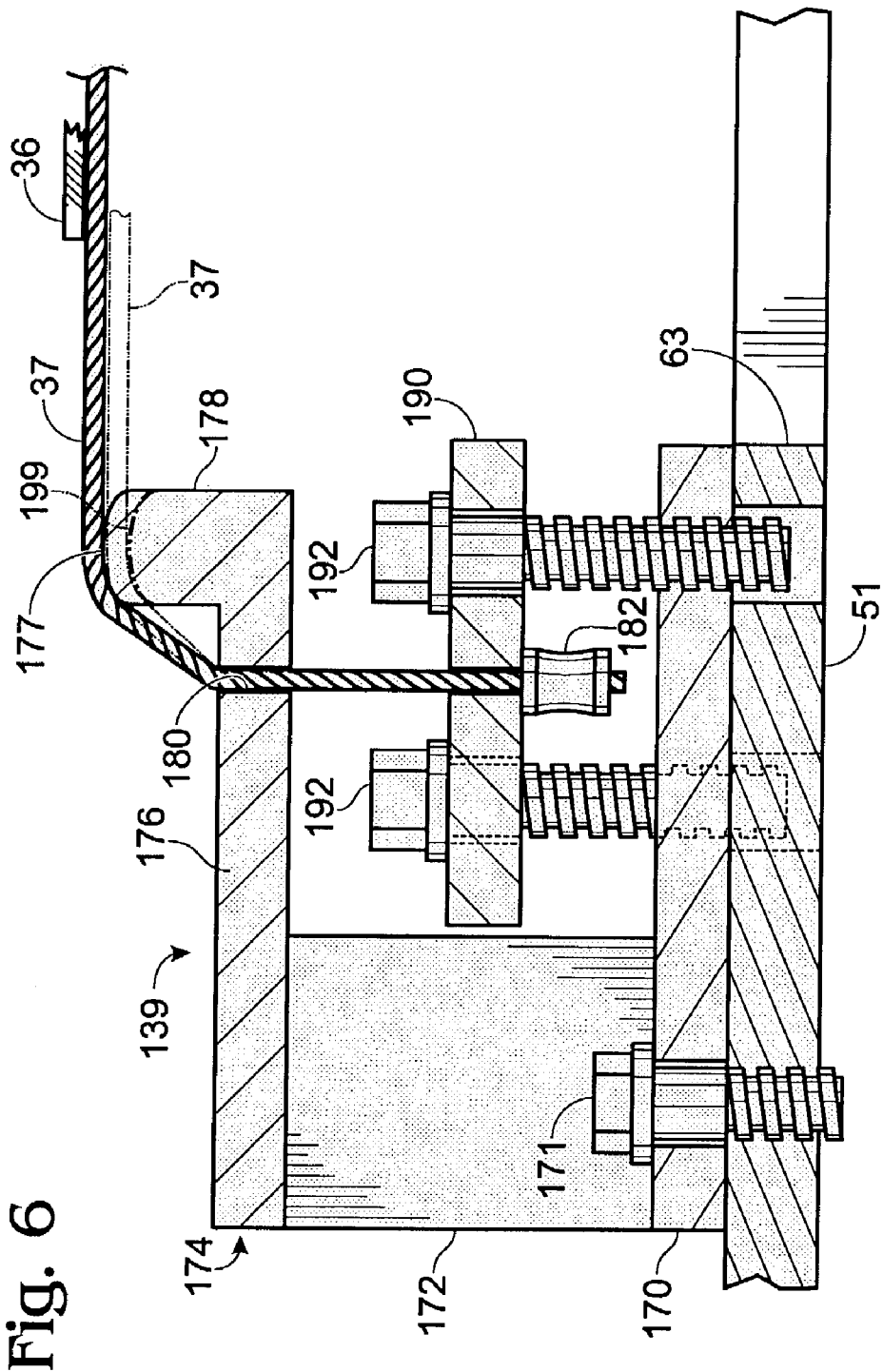
FIG. 6 is an enlarged, detailed section view showing an alternative embodiment of part of the sample holder of the present invention.

FIG. 6 depicts a way of anchoring the ends of the support wires 37 so that the entire set of wires can be tensioned and released by adjusting a movable tension plate 190 to which the ends are fastened. In this embodiment, the beam assembly 139 comprises a base plate 170 that is attached close to an edge of the opening 63 in the top 51. That plate may be attached by attachment bolts 171, for example, that can be removed to permit the detachment of the entire assembly 139 from the cabinet 49. In this regard, a beam assembly substantially identical to the fixed beam assembly 39 of FIG. 4, or like the assembly 41 of FIG. 5, may be used on the opposite edge of the window 63 to fasten the other ends of the wires.

A number of spacer plates 172 are fixed to the upper surface of the base plate 170 to extend therefrom and support an anchor plate 174 above the base plate 170. The anchor plate 174 is generally "L" shaped with a flat leg 176 that extends inwardly beyond the spacers 172 and terminates in an upwardly projecting flange 178.

The uppermost edge 177 of the flange 178 is rounded. One end of each of the wires 37 mentioned above is passed through an aperture 180 made in the inwardly projecting section of the leg 176 and then through a hole in the center of a rigid tension plate 190 that is located between the top 51 of the cabinet and the inwardly extending part of the anchor plate 174. The ends of the wire are captured in stop sleeves 182, which, like sleeves 82 in the earlier described embodiment are crimped to fix the sleeve to the wire end. Similarly, since the sleeve diameter exceeds that of the aperture in the tension plate, the wire 37 can thereafter be tensioned with the sleeve abutting the underside of that plate 190.

It is contemplated that grooves, such as shown at 199 in FIG. 6, may be formed in the top edge 177 of the beam assembly (as well as in the earlier discussed edges 77, 97) and sized to receive the wires 37 thereby to permit and maintain proper spacing of the wires.

A few spaced-apart tension-adjusting, shoulder-type bolts 192 are passed through clear holes in the tension plate and threaded into the base plate 170. It will be appreciated, therefore, that the threading and unthreading of these few bolts 192 will respectively increase and decrease the tension in all of the wires 37. It will also be understood that with the ends of the wires captured as a single set in a single rigid bar member or the like, any of a number of quick release clamping mechanisms could be used for tensioning and releasing the set of wires. Moreover, any of a number of mechanisms can be employed for securing the anchor plate 174 to the cabinet while permitting motion of the tension plate. For example, one can do away with the bolts 192 and connect, via a hinge, a long edge of the plate 190 to the cabinet or to the base plate 170. A handle can be attached to the plate for moving the plate about the hinge to simultaneously tighten and loosen all of the wires. A toggle or latch mechanism could be included to secure the plate in the wires-tightened position.

Although preferred and alternative embodiments of the present invention have been described, it will be appreciated that the spirit and scope of the invention is not limited to those embodiments, but extend to the various modifications and equivalents. For example, although the sample holder was discussed above in the context of a birefringence measurement system, it will be understood that the holder can be adapted for use in any of a variety of optical setups or systems.

Moreover, although the focus here was on a large-format sample, it will be appreciated that the holder of the present invention will also be useable with samples of any size, including quite small ones, without the need for modifying the holder.

What is claimed is:

1. A method of supporting a sample in an optical setup that directs a beam of light through the sample, comprising the step of:
   supporting the sample on a plurality of spaced apart elongated members that are arranged to define a plane for supporting the sample and so that the elongated members do not cross one another.

2. A method of supporting a sample in an optical setup that directs a beam of light through the sample, comprising the step of:
   supporting the sample on a plurality of spaced apart elongated members; and
   tensioning the elongated members so that the tensioned members align to provide a flat surface for supporting the sample.

3. The method of claim 1 including the step of moving components of the optical setup relative to the sample for directing the light beam through different parts of the sample.

4. An optical element support apparatus, comprising:
   two spaced-apart anchor members; and
   a plurality of elongated members, each member being mounted for rotation about its long axis between the anchor members, and the elongated members being spaced from each other to provide support for the optical element.

5. An optical element support apparatus, comprising:
   two spaced-apart anchor members;
   a plurality of elongated members secured between the anchor members and spaced from each other to provide support for the optical element; and
   wherein the elongated members are tensioned between the anchor members in a manner such that the elongated members are held in a common plane.

6. The apparatus of claim 5 wherein the elongated members are wires.

7. A method for measuring the birefringence over the area of a large-format sample that has at least one flat surface, wherein the birefringence measurement requires a light source and a detector, the method comprising the steps of:
   positioning the flat surface of the sample on a plurality of elongated members that are arranged in a plane to support the flat surface; and
   moving the source and detector together relative to the sample and across the area of the sample so that the flat supported surface of the sample is located between the source and the detector.

8. The method of claim 7 including the step of tensioning the elongated members.

9. The method of claim 8 including the step of providing wires as the tensioned elongated members.

10. The method claim 9 including the step of simultaneously tightening or loosening all of the plurality of wires.

11. The method of claim 7 wherein the supporting step includes supporting the sample on a plurality of elongated members that are rotatable about their long axes.

12. The method of claim 7 including the step of arranging the elongated members to be parallel.

13. The method of claim 7 including the step of supporting the sample in a substantially horizontal plane.

14. The method of claim 7 including the step of supporting the sample on a plurality of elongated members that do not contact one another.

15. The apparatus of claim 5 including tensioning means for selectively releasing and applying tension to the elongated members.

16. The apparatus of claim 15 wherein the tensioning means includes clamp means for selectively releasing and applying tension simultaneously to all of the elongated members.

* * * * *